US011261476B2

(12) United States Patent
Klintstedt et al.

(10) Patent No.: US 11,261,476 B2
(45) Date of Patent: Mar. 1, 2022

(54) METHOD FOR RECOVERING MICROBIAL CELLS

(71) Applicant: Q-linea AB, Uppsala (SE)

(72) Inventors: Markus Klintstedt, Uppsala (SE); Harer Osman, Uppsala (SE); Mats Gullberg, Sollentuna (SE)

(73) Assignee: Q-LINEA AB, Uppsala (SE)

( * ) Notice: Subject to any disclaimer, the term of this patent is extended or adjusted under 35 U.S.C. 154(b) by 252 days.

(21) Appl. No.: 16/341,809

(22) PCT Filed: Oct. 19, 2017

(86) PCT No.: PCT/EP2017/076707
§ 371 (c)(1),
(2) Date: Apr. 12, 2019

(87) PCT Pub. No.: WO2018/073342
PCT Pub. Date: Apr. 26, 2018

(65) Prior Publication Data
US 2019/0316173 A1 Oct. 17, 2019

(30) Foreign Application Priority Data
Oct. 19, 2016 (GB) ..................... 1617713

(51) Int. Cl.
C12Q 1/24 (2006.01)
C12M 1/40 (2006.01)
C12M 1/26 (2006.01)
G01N 1/40 (2006.01)

(52) U.S. Cl.
CPC .............. *C12Q 1/24* (2013.01); *C12M 21/18* (2013.01); *C12M 33/14* (2013.01); *G01N 1/4005* (2013.01); *G01N 1/4077* (2013.01); *G01N 2001/4016* (2013.01); *G01N 2001/4088* (2013.01)

(58) Field of Classification Search
CPC ............ C12Q 1/24; C12N 1/20; C12M 33/14; C12M 21/18; G01N 1/4077; G01N 1/4005; G01N 2001/4016; G01N 2001/4088
See application file for complete search history.

(56) References Cited

U.S. PATENT DOCUMENTS

| 5,587,286 | A | 12/1996 | Pahuski et al. |
| 5,789,173 | A | 8/1998 | Peck et al. |
| 7,547,526 | B2 | 6/2009 | Ladisch et al. |
| 8,460,887 | B2 | 6/2013 | Goldberg et al. |
| 8,481,265 | B2 | 7/2013 | Peytavi et al. |
| 8,603,769 | B2 | 12/2013 | Feng et al. |
| 8,652,800 | B2 | 2/2014 | Walsh et al. |
| 2002/0148729 | A1 | 10/2002 | Armstrong |
| 2005/0014128 | A1 | 1/2005 | Ewert et al. |
| 2005/0095665 | A1 | 5/2005 | Williams et al. |
| 2005/0244943 | A1 | 11/2005 | Ladisch et al. |
| 2006/0154247 | A1 | 7/2006 | Baker et al. |
| 2008/0131955 | A1 | 6/2008 | Stone |
| 2009/0004727 | A1 | 1/2009 | Ehrenfeld Stolzenbach et al. |
| 2009/0064809 | A1 | 3/2009 | Miret et al. |
| 2009/0326211 | A1 | 12/2009 | Boyette et al. |
| 2010/0120085 | A1 | 5/2010 | Hyman et al. |
| 2010/0124763 | A1 | 5/2010 | Walsh et al. |
| 2010/0143964 | A1 | 6/2010 | Mor et al. |
| 2010/0184210 | A1 | 7/2010 | Rossmanith et al. |
| 2010/0255573 | A1 | 10/2010 | Bond et al. |
| 2010/0288060 | A1 | 11/2010 | Ronsick et al. |
| 2012/0122110 | A1 | 5/2012 | Rossmanith et al. |
| 2012/0231446 | A1 | 9/2012 | Heckel et al. |
| 2013/0045532 | A1 | 2/2013 | Hyman et al. |
| 2013/0171615 | A1 | 7/2013 | Van Meerbergen et al. |
| 2014/0017062 | A1 | 1/2014 | Turner et al. |
| 2014/0087361 | A1 | 3/2014 | Dobbelaer et al. |
| 2014/0186832 | A1 | 7/2014 | Fuchs et al. |
| 2014/0278136 | A1 | 9/2014 | Shamsheyeva et al. |

(Continued)

FOREIGN PATENT DOCUMENTS

| EP | 1 867 973 A1 | 12/2007 |
| EP | 1 527 172 B1 | 11/2008 |
| EP | 2 049 677 B1 | 7/2011 |

(Continued)

OTHER PUBLICATIONS

Goyal, S., Gerba, C. Simple Method for Concentration of Bacteria from Large Volumes of Tap Water. Applied and Environmental Microbiology. (1980). 40(5); 912-916 (Year: 1980).*

Hasegawa H, et al. Membrane filter (pore size, 0.22-0.45 micro m; thickness, 150 micro m) passing-through activity of Pseudomonas aeruginosa and other bacterial species with indigenous infiltration ability. FEMS Microbiol Lett. Jun. 6, 2003;223(1):41-6 (Year: 2003).*

Mayrl, E. et al. Broad Range Evaluation of the Matrix Solubilization (Matrix Lysis) Strategy for Direct Enumeration of Foodborne Pathogens) by Nucleic Acids Technologies. Journal of Food Protec, International Association for Food Protection, US. 2009. 72(6) 1225-1233 (Year: 2009).*

Merriam-Webster, definition of "Polyamide." https://www.merriam-webster.com/dictionary/polyamide. Accessed Feb. 12, 2021 (Year: 2021).*

(Continued)

*Primary Examiner* — Sean C. Barron
(74) *Attorney, Agent, or Firm* — Fay Sharpe, LLP

(57) ABSTRACT

The present invention provides a method of recovering viable microbial cells from a complex sample, said method comprising: a) providing a sample having a volume of at least 1 ml; b) contacting said sample with a buffer solution and one or more proteases, wherein said buffer solution has a pH of at least pH 6 and less than pH 11, wherein said buffer solution and said one more proteases do not comprise a detergent or a chaotrope, and wherein the buffer solution/protease/sample mixture is non-hypotonic; c) filtering the mixture obtained in step (b) through a filter suitable for retaining microbial cells; and d) recovering the microbial cells retained by the filter in step (c), wherein the recovered microbial cells are viable, and a microbial recovery device for the same.

19 Claims, No Drawings

(56) References Cited

U.S. PATENT DOCUMENTS

| | | | |
|---|---|---|---|
| 2014/0335522 | A1 | 11/2014 | Menard et al. |
| 2015/0132793 | A1* | 5/2015 | Penterman .............. C12Q 1/24 435/30 |

FOREIGN PATENT DOCUMENTS

| | | |
|---|---|---|
| EP | 2 718 713 A1 | 4/2014 |
| EP | 2 510 123 B1 | 9/2014 |
| WO | WO 02/31184 A2 | 4/2002 |
| WO | WO 2008/017097 A1 | 2/2008 |
| WO | WO 2008/152888 A1 | 12/2008 |
| WO | WO 2010/062352 A1 | 6/2010 |
| WO | WO 2010/145754 A1 | 12/2010 |
| WO | WO 2011/068465 A1 | 6/2011 |
| WO | WO 2012/088412 A2 | 6/2012 |
| WO | WO 2012/143661 A1 | 10/2012 |
| WO | WO 2012/168003 A1 | 12/2012 |
| WO | WO 2013/091102 A1 | 6/2013 |
| WO | WO 2014/040088 A1 | 3/2014 |
| WO | WO 2015/044191 A1 | 4/2015 |
| WO | WO 2015/179976 A1 | 12/2015 |
| WO | WO 2015/189390 A1 | 12/2015 |
| WO | WO 2016/207065 A1 | 12/2016 |

OTHER PUBLICATIONS

NEB (New England Biolabs, Proteinase K information web page from 2015. PDF copy provided) (Year: 2015).*

Neves, L., Marra, A.R., Camargo, T.Z.S. et al. Correlation between mass and volume of collected blood with positivity of blood cultures. BMC Res Notes (2015). 8, 383 (Year: 2015).*

Smith, L. et al. Comparison of Membrane Filters for Recovery of Legionellae from Water Samples. Applied and Environmental Microbiology. (1993). 59(1); p. 344-346 (Year: 1993).*

Arias, Mauricio et al., "Red Blood Cell Permeabilization By Hypotonic Treatments, Saponin, And Anticancer Avicins", Biochimica et Biophysica Acta, 1798 (2010) p. 1189-1196.

Baker, Zelma et al., "The Bactericidal Action Of Synthetic Detergents", Walter G. Zoller Memorial Dental Clinic, The Department of Bacteriology and Parasitology, and The Department of Medicine, The University of Chicago, Chicago, (1941) p. 611-620.

Banada, Padmapriya P. et al., "Highly Sensitive Detection Of *Staphylococcus aureus* Directly From Patient Blood", PloS One, vol. 7, Issue 2, e31126 (Feb. 2012) p. 1-7.

Biological Buffers, AppliChem, 2008, 20 pages.

Boardman, Anna K. et al., "Rapid Microbial Sample Preparation From Blood Using A Novel Concentration Device", PloS One, vol. 10, Issue 2, e0116837 (Feb. 2015) p. 1-13.

Broeren, M. A. C. et al., "Antimicrobial Susceptibility Testing In 90 Min By Bacterial Cell Count Monitoring", Clinical Microbiology And Infection, vol. 19, No. 3 (Mar. 2013) p. 286-291.

Chapin, Kimberle C. et al., "Direct Susceptibility Testing Of Positive Blood Cultures By Using Sensititre Broth Microdilution Plates", Journal of Clinical Microbiology, vol. 41, No. 10 (Oct. 2003) p. 4751-4754.

Cotter, Paul D. et al., "Surviving The Acid Test: Responses Of Gram-Positive Bacteria To Low PH", Microbiology And Molecular Biology Reviews, vol. 67, No. 3 (Sep. 2003) p. 429-453.

De Jong, Ymke, "A Fast Antibiotic Susceptibility Test By Direct Staining", Thesis Report, Uppsala Universitet, (Spring 2014) p. 1-23.

Decision Summary BIOFIRE—FilmArray Blood Culture Panel (2013) 72 pages.

Farina, Claudio et al., "Direct Identification Of Microorganisms From Positive Blood Cultures Using The Lysis-Filtration Technique And Matrix-Assisted Laser Desorption Ionization Time-Of-Flight Mass Spectrometry (MALDI-TOF MS): A Multicentre Study", New Microbiologica, 38 (2015) p. 245-250.

Li, Xuan et al., "Rapid Sample Processing For Detection Of Food-Borne Pathogens Via Cross-Flow Microfiltration", Applied and Environmental Microbiology, vol. 79, No. 22 (Nov. 2013) p. 7048-7054.

Maertens, Johan A. et al., "Diagnosis Of Fungal Infections", Informa Healthcare (2007) cover page and p. 135.

Mayrl, Eva et al., "Broad Range Evaluation Of The Matrix Solubilization (Matrix Lysis) Strategy For Direct Enumeration Of Foodborne Pathogens By Nucleic Acids Technologies", Journal of Food Protection, vol. 72, No. 6 (2009) p. 1225-1233.

Metzger, Steven et al., "Rapid Simultaneous Identification And Quantitation Of *Staphylococcus aureus* And Pseudomonas Aeruginosa Directly From Bronchoalveolar Lavage Specimens Using Automated Microscopy", Diagnostic Microbiology And Infectious Disease, 79 (2014) p. 160-165.

Padan, Etana et al., "Alkaline pH Homeostasis In Bacteria: New Insights", Biochimica et Biophysica Acta, 1717 (2005) p. 67-88.

Palarasah, Yaseelan et al., "Sodium Polyanethole Sulfonate As An Inhibitor Of Activation Of Complement Function In Blood Culture Systems", Journal Of Clinical Microbiology, vol. 48, No. 3 (Mar. 2010) p. 908-914.

Peterkin, Pearl I. et al., "Membrane Filtration Of Dairy Products For Microbiological Analysis", Applied And Environmental Microbiology, vol. 39, No. 6 (Jun. 1980) p. 1138-1143.

Price, Connie S. et al., "Rapid Antibiotic Susceptibility Phenotypic Characterization Of *Staphylococcus aureus* Using Automated Microscopy Of Small Numbers of Cells", Journal Of Microbiological Methods, 98 (2014) p. 50-58.

Rajagopal, Soumitra et al., "Eight Gram—Negative Bacteria Are 10 000 Times More Sensitive To Cationic Detergents Than To Anionic Detergents", Can. J. Microbiol., vol. 49 (2003) p. 775-780.

Regan, John F. et al., "Technical Advance—A Sample Extraction Method For Faster, More Sensitive PCR-Based Detection Of Pathogens In Blood Culture", The Journal Of Molecular Diagnostics, vol. 14, No. 2 (Mar. 2012) p. 120-129.

Shamsheyeva, Alena et al., "Evaluation Of An Antimicrobial Susceptibility Testing Algorithm To Determine Minimum Inhibitory Concentration Using Growth Of Immobilized Staphylococcal Cells Measured By Automated Microscopy", ASM Conference 2014, 1 page.

Vibbert, Hunter B. et al., "Accelerating Sample Preparation Through Enzyme-Assisted Microfiltration Of Salmonella In Chicken Extract", American Institute Of Chemical Engineers, Biotechnol. Prog., vol. 31, No. 6 (2015) p. 1551-1562.

Villarreal, Jessica Varela et al., "DNase I And Proteinase K Eliminate DNA From Injured Or Dead Bacteria But Not From Living Bacteria In Microbial Reference Systems And Natural Drinking Water Biofilms For Subsequent Molecular Biology Analyses", Journal of Microbiological Methods, 94 (2013) p. 161-169.

Wada, Atsushi et al., "Rapid Discrimination Of Gram-Positive And Gram-Negative Bacteria In Liquid Samples By Using NaOH-Sodium Dodecyl Sulfate Solution And Flow Cytometry", PloS One, vol. 7, Issue 10, e47093 (Oct. 2012) p. 1-10.

International Search Report and Written Opinion of International Application No. PCT/EP2017/076707 dated Dec. 6, 2017, 14 pages.

United Kingdom International Patent Office Search Report of British Application No. GB1518463.3 dated Jul. 22, 2016, 2 pages.

\* cited by examiner

METHOD FOR RECOVERING MICROBIAL CELLS

The present invention relates to methods for recovering viable microorganisms (microbial cells) from large volumes of a complex sample. In particular, the sample may be or may comprise a clinical sample, especially blood e.g. a blood sample in a blood culture flask. The present invention is based on the surprising discovery that the addition of certain buffer solutions, particularly simple buffer solutions comprising a protease, enhances the filterability of complex samples. This allows for the rapid and efficient recovery of viable microorganism cells from complex samples for subsequent identification and biochemical testing.

Microbial infections represent a major class of human and animal disease with significant clinical and economic implications. Whilst various classes and types of antimicrobial agents are available to treat and/or prevent microbial infections, antimicrobial resistance is a large and growing problem in modern medicine. The numbers of antimicrobial-resistant strains of various microbial pathogens have proliferated in the past 20 years, and microorganisms continue to develop resistance to a growing number of antimicrobial, particularly antibiotic, classes. With the spread of resistance mechanisms to more organisms, the public health impact and costs associated with antimicrobial resistance are projected to increase rapidly in the years to come. In the context of treatment of a microbial infection, it can therefore be desirable, and indeed important, to have information regarding the nature of the infecting microorganism and its antimicrobial susceptibility profile in order both to ensure effective treatment and also to reduce the use of unnecessary or ineffective antibiotics and thereby to help control the spread of antibiotic, or more generally antimicrobial, resistance. This is particularly so in the case of serious or life-threatening infections in which rapid effective treatment is vital.

Sepsis, a potentially fatal whole-body inflammation caused by severe infection is the most expensive condition and driver of hospital costs in the US, comprising 5% of the total national hospital cost. Mortality increases 7% for every hour for severe sepsis, if not treated properly, and the rising prevalence of antimicrobial-resistant sepsis causing strains makes predictions of the correct treatment for sepsis increasingly difficult. The current gold standard for diagnosis of the microorganisms causing sepsis is based on phenotypic and biochemical identification techniques which require the isolation and culture of pure cultures of the infecting microorganisms. It can take several days to perform the microbial identification (ID) and antibiotic susceptibility (AST) tests to identify the infection and determine the susceptibility profile of antimicrobial resistant microorganisms. Current clinical practice requires treatment with a broad-spectrum antibiotic within 1 hour of suspicion of sepsis based on clinical symptoms. A second dose is required within 6-8 hours and this administration is continued every sixth to eighth hour until identification of the microorganism and its antibiotic susceptibility (ID/AST) is established.

Due to the lethal condition of sepsis physicians are unwilling to change treatment from broad-spectrum antibiotics initially if the patient experiences a clinical response until the nature of the microbial infection is determined and antimicrobial susceptibility established. This in turn leads to the unnecessarily high use of broad spectrum antibiotics, in turn fuelling the rise of antimicrobial resistance among microorganisms.

Conventional testing methods utilise turbidity measurements or disc diffusion to assess the effect of antimicrobial agents on microorganism growth, and traditional biochemical and microbiological techniques to identify a microorganism. These techniques can take several days to identify and characterise a microorganism in a clinical sample, due to the requirement for prolonged periods of incubation to allow microbial growth.

Various different techniques that reduce the time between sample collection and diagnosis have been developed in recent years.

Methods of rapid microbial identification are described in US 2010/0124763, in which microbial cultures are enriched and microorganisms identified spectroscopically.

Rapid susceptibility testing techniques using flow cytometry (Broeren et al. 2013 Clin Microbiol Infect 19, 286-291) and automated microscopy (Price et al. 2014 JMM. 98 50-59) have been developed to reduce the time required for incubation prior to susceptibility being determined. The systems developed by Accelerate Diagnostics use imaging of the growth of individual cells or colonies on a surface to monitor microbial growth in the presence of an antibiotic in AST tests (see for example WO2014/040088, US 2014/0278136 and U.S. Pat. No. 8,460,887). Quantitative PCR of microbial DNA has also been used as a measure for microbial growth to determine antimicrobial susceptibility, as described in U.S. Pat. No. 5,789,173.

Combined microorganism identification and susceptibility testing methods have also been developed. Described in US 2005/0095665 is a system in which panels of selected growth media and chromogenic and fluorogenic substrates are used in combination with turbimetric measurement of microbial growth in an automated microtiter well format to identify microorganisms and determine antimicrobial susceptibility. Automated microscopy methods have also been developed (Metzger et al. 2014 Diagnostic Microbiology and Infectious Disease 79 160-165). The BD Phoenix™ system also allows for the rapid simultaneous identification and characterisation of microorganisms, and utilises a variety of chromogenic and fluorogenic substrates to identify microorganisms in a sample and monitor microbial growth to determine the antimicrobial susceptibility of microorganisms in a sample.

As a result of these and other advances, the time required to obtain a diagnosis from a patient sample has fallen dramatically in recent years. However, despite this, methods which can help reduce further still the time between sample collection and diagnosis are required in order to further improve the prognosis of patients.

Microbial cells may be present in clinical samples in concentrations as low as 1 CFU/ml, and thus clinical samples are typically incubated for a period of time prior to testing in order to obtain a sufficient quantity of microbial cells for testing to take place. As discussed above, this can result in delays in diagnosis. This problem may be addressed by recovering microbial cells from cultures which have been cultured for a reduced period of time (and which therefore contain fewer microbial cells than those cultured for longer), or indeed by recovering microbial cells directly from a clinical sample without a prior culture step, thereby effectively increasing the effective concentration of microbial cells present in a sample. This does however mean that (to obtain a sufficient number of microbial cells for testing) microbial cells need to be recovered from larger volumes of sample, e.g. from several ml of sample, and in the context of complex samples this can give rise to problems in recovery of the microbial cells, particularly where recovery by filtration is desired, which is advantageously the case in automated systems.

Microorganisms in a clinical sample or clinical sample culture may be enriched by various means, thereby bypassing the requirement for long periods of incubation. Microbial cells can be enriched from clinical samples by the selective lysis of non-microbial cells, e.g. cells derived from the subject under test (from whom a clinical sample is obtained), followed by the recovery of microbial cells from the sample, typically by filtration or centrifugation. Methods for enriching microbial cells from clinical samples or clinical sample cultures utilising lysis buffers comprising a range of lytic agents including saponins (U.S. Pat. No. 8,481,265), non-ionic detergents (EP2510123), ionic detergents (EP2718713), choline (U.S. Pat. No. 8,603,769) and chaotropes (US 2012/0231446) are known in the art, as are methods relying on hypotonic lysis of cells, e.g. blood cells. Further methods which utilise harsh alkaline conditions are also known in the art (Banada et al. 2012. PLoS One 7, e31126), but such methods do not recover viable microbial cells; lysis of microbial cells is known to occur at higher pH values (e.g. at pH11 and above).

In contrast to this, the present invention provides methods for the recovery of viable microbial cells from complex samples, such as a clinical sample, by filtration without the use of lysis buffers containing detergent, chaotrope(s) and/or choline or, in some embodiments, any other lytic agents. Indeed, it has surprisingly been found that complete or total selective lysis of non-microbial cells present in the sample is not required. Whilst selective non-microbial cell lysis may occur at increased pH (e.g. at pH9.5 or above), and this is included in the scope of the invention, it has surprisingly been found that this is not a requirement of the methods of the present invention. In other words, it has been found that a large volume of a complex sample may, surprisingly, be filtered without the filter clogging, to recover microorganisms, even in the absence of the complete selective lysis, (or significant lysis) of non-microbial cells present in the sample.

The present invention is based on the surprising discovery that treatment of clinical sample with buffer solutions comprising a protease, but which do not comprise detergents or chaotropes can be sufficient to increase the volume of clinical samples that can be filtered (i.e. without the filter clogging before the whole volume of sample is passed through), thereby improving the recovery of microbial cells present therein. In particular, the methods of the present invention are based on the discovery that in certain pH ranges and in the presence of a protease, the filterability (i.e. the degree to which a sample may be filtered) can be dramatically increased without significantly harming the viability of the microbial cells in the sample. In other words, the methods of the present invention allow a greater volume of sample to be filtered per unit area of filter, thereby increasing the volume of a clinical sample that can be filtered, and the number of viable microbial cells that can be recovered from a clinical sample. Microbial cells recovered from a clinical sample, may therefore be cultured further following this method and/or subjected to antimicrobial susceptibility testing.

Although this surprising effect was first observed with clinical samples, and in particular clinical sample cultures, it is apparent that the methods for increasing the filterability of a sample may be applied more generally to any complex sample, and in particular any complex sample which is hard to filter and/or which contains non-microbial cells.

Accordingly, in a first aspect the present invention provides a method of recovering viable microbial cells from a complex sample, said method comprising:
 a) providing a complex sample having a volume of at least 1 ml;
 b) contacting said sample with a buffer solution and one or more proteases, wherein said buffer solution has a pH of at least pH 6 and less than pH 11, wherein said buffer solution and said one more proteases do not comprise a detergent or a chaotrope, and wherein the buffer solution/protease/sample mixture is non-hypotonic;
 c) filtering the mixture obtained in step (b) through a filter suitable for retaining microbial cells; and
 d) recovering the microbial cells retained by the filter in step (c), wherein the recovered microbial cells are viable.

The method of the invention thus provides a method for recovering viable microbial cells from a large volume of a complex sample. "Large" is defined herein to mean at least 1 ml. More particularly, the sample may have a volume of greater than 1 ml or equal to ($\geq$) 2 ml, or greater than 2, 3, 4, 5, 6, 8, or 9 ml. Expressed in another way, the sample may have a volume of at least 2, 3, 4, 5, 6, 7, 8, 9 or 10 ml. The sample volume may also be at least 15 ml, 20 ml, 30 ml, 40 ml or 50 ml, or more. For example the sample volume may be at least 2 ml, at least 5 ml or at least 10 ml.

It will be understood that step (b) may include adding the buffer solution and protease(s) to the sample (e.g. to a vessel or container containing the sample), or adding the sample to the buffer solution and/or proteases (e.g. to a vessel or container containing the buffer solution and/or protease(s)). The buffer solution and one or more proteases may be pre-mixed and added to the sample (or vice versa). This may include that the buffer solution and protease(s) are provided (e.g. prepared and stored) as a mixture, or that the buffer solution and protease(s) are provided (e.g. prepared and stored) separately and are pre-mixed in use e.g. prior to contacting with the sample. Alternatively, the buffer solution and one or more proteases may be added to the sample separately, at the same time (simultaneously) or sequentially, in any order. Thus the buffer solution and protease(s) may in one embodiment be mixed during use. Alternatively, the buffer solution, sample and protease(s) may be mixed during use.

The buffer solution and proteasel(s) may be provided (e.g. stored) in different formats. For example the protease(s) may be provided as a solid or powder (e.g. lyophilised or freeze-dried). As described in more detail below, such a powder protease preparation may be reconstituted prior to or during use, e.g. with the buffer solution, or with the sample, or both. Alternatively, the protease preparation may be provided as a solution for contact with the sample, e.g. in a buffer solution or other aqueous solution, for example in a buffer which is the same as the buffer solution of step (b).

Step (b) may comprise contacting the sample with the buffer solution and protease(s) and incubating the (resulting) buffer solution/protease/sample mixture. The term "incubating" is used broadly herein to mean contacting the buffer solution and protease(s) with the sample. Thus the term includes simply allowing the buffer solution/protease/sample mixture to stand for a period of time before filtering in step (c). The sample/buffer solution/protease mixture may be mixed e.g. after addition of the buffer solution and protease(s) to the sample, and/or during the incubation. The time of incubation may therefore vary e.g. from a minute, or a few minutes or less to longer of periods of time e.g. for 5, or 10 minutes or more. Thus, by way of representative example, the buffer solution may be added to the sample and the mixture may be incubated for at least 1, 2, 3, 4, 5, 6, 7, 8, 9, 10, 12, or 15 minutes or more. Longer incubation times e.g. 20 or 30 minutes or more are possible, but may not be necessary or desirable. It will be understood in this respect, that the process of filtration in step (c) may take some time and so incubation could take place during the filtration step. For example, the sample may be contacted with buffer solution and protease(s) and the process of filtration may be started immediately or almost immediately (e.g. after a minute, or less). Incubation of the sample with the buffer solution and protease(s) may take place or may continue during the filtration step. In some embodiments incubation may be performed at room temperature and in other embodiments temperature may be increased. Thus, incubation may be performed at e.g. 15 to 37° C., for example at any one of 15, 18, 20, 22 or 25° C. to any one of 30, 35, or 37° C.

It will be understood from the above that the sample/buffer solution/protease mixture may be obtained in various ways depending upon the order of addition and whether or not the buffer solution and protease(s) are pre-mixed before contacting with the sample. Thus in one embodiment the buffer solution may contain one or more proteases. After the contacting step (b) such a protease-containing buffer solution is also referred to herein as a buffer solution. The term "buffer solution/protease/sample" mixture" may be used with the components of the mixture presented in any order and is synonymous in meaning, and used interchangeably, with the term "buffer solution/sample mixture".

When the buffer solution and protease(s) are added to the sample the resulting mixture is non-hypotonic. As will be described in more detail below, the buffer solution/protease/sample mixture is in particular non-hypotonic with respect to the complex sample (i.e. with respect to the starting sample, or the sample before it is subjected to the method, or before the buffer solution/proteases are added) and more particularly with respect to any non-microbial cells which may be contained in the sample (e.g. cells from the test subject present in a clinical sample from a test subject). Accordingly, the composition of the buffer solution is such that the buffer solution/protease/sample mixture (i.e. the mixture formed by adding the buffer solution and protease(s) to the sample) is non-hypotonic. Likewise, the protease(s) are provided or prepared in such a way that the resulting mixture is non-hypotonic.

As discussed above, it may be the case that not all the non-microbial cells present in the sample are lysed during the methods of the present invention, and a fraction of the non-microbial cells present in the complex sample may thus also be retained on the filter in step (c) of the present method. Thus, whilst at least a portion of the non-microbial cells present in the sample may be lysed by the methods described herein, it may be the case that the degree of lysis will not be sufficient to remove all or a substantial portion of the non-microbial cells present in the sample. The degree or amount of lysis of non-microbial cells may vary, depending on the sample, the subject the sample is taken from (for a clinical sample), the precise nature of the buffer solution (including e.g. the pH), the precise nature of the protease etc. Thus, rather than providing a method that relies on or requires the complete, or substantially complete lysis of non-microbial cells for the selective enrichment or isolation of microbial cells from a sample relative to the non-microbial cells present in the sample (i.e. a selective lysis method), the present method may instead be viewed as providing a cheap, simple and effective method for recovering the cellular components (and in particular microbial cells) from a sample by allowing the sample to be more-easily filtered in order to remove its liquid components.

The term "lysing" means breaking down of a cell, and in particular breaking down a cell to release cell contents, including particularly nucleic acid (i.e. disrupting a cell membrane). Lysis may typically be achieved by any means, a vast number of which are known in the art, for example viral, enzymatic, mechanical, electrical, chemical, heat, cold or osmotic mechanisms that compromise cell integrity leading to the partial or full release of cellular components into surrounding solution.

The term "selectively lysing" or "selective lysis" means lysing of a particular subset of the cells present in a sample. Thus selective lysis conditions are conditions which are designed to lyse (i.e. which target) only a particular subset of cells present in a sample. For instance, as described above selective lysis may be of non-microbial cells, or more particularly the cells which derive from the subject under test (e.g. mammalian cells) that are present in a clinical sample, without substantially lysing the microbial cells present in a clinical sample.

Alternatively presented, the present invention may be viewed as providing improved methods for the recovery of viable microbial cells from a sample by enhancing its filterability. Liquid components and unwanted smaller components (e.g. cellular or other debris, unwanted molecules and compounds etc.) of the sample are removed by filtration (the filtrate) whilst cellular material, including microbial cells (the retentate) is retained on a filter membrane. Microbial cells that are retained following filtration may subsequently be recovered.

Put another way, the present invention may be viewed as providing improved methods for removing the liquid components of a sample (including soluble and suspended components) from the cellular components of the sample. Samples collected (e.g. from a subject or patient, i.e. a clinical sample) may contain components (e.g. antimicrobial compounds such as antibiotics) which may interfere with or inhibit tests (e.g. identification or AST tests) which might be performed on the microbial cells obtained in a sample. Filtration of a sample to remove the liquid component may therefore enhance the accuracy and/or sensitivity of subsequent testing methods.

The methods of the present invention may be used to recover any microbial cell from a sample. The terms microbial cell and microorganism are used interchangeably herein, and may both be used to encompass any organism which may fall under the category of "microorganism". Although not necessarily so, microorganisms may be unicellular, or may have a unicellular life stage. The microorganism may be prokaryotic or eukaryotic and generally will include bacteria, archaea, fungi, algae, and protists, including notably protozoa. Of particular interests are bacteria, which may be Gram-positive or Gram negative or Gram-indeterminate or Gram-non-responsive, and fungi.

Particularly, clinically relevant genera of bacteria include *Staphylococcus* (including Coagulase-negative *Staphylococcus*), *Clostridium, Escherichia, Salmonella, Pseudomonas, Propionibacterium, Bacillus, Lactobacillus, Legionella, Mycobacterium, Micrococcus, Fusobacterium, Moraxella, Proteus, Escherichia, Klebsiella, Acinetobacter, Burkholderia, Entercoccus, Enterobacter, Citrobacter, Haemophilus, Neisseria, Serratia, Streptococcus* (including Alpha-hemolytic and Beta-hemolytic Streptococci), *Bacteroides, Yersinia,* and *Stenotrophomas,* and indeed any other enteric or coliform bacteria. Beta-hemolytic Streptococci would include Group A, Group B, Group C, Group D, Group E, Group F, Group G and Group H Streptococci.

Non-limiting examples of Gram-positive bacteria include *Staphylococcus aureus, Staphylococcus haemolyticus, Staphylococcus epidermidis, Staphylococcus saprophyticus, Staphylococcus lugdunensis, Staphylococcus schleiferei, Staphylococcus caprae, Staphylococcus pneumoniae, Staphylococcus agalactiae Staphylococcus pyogenes, Staphylococcus salivarius, Staphylococcus sanguinis, Staphylococcus anginosus, Streptococcus pneumoniae, Streptococcus pyogenes, Streptococcus mitis, Streptococcus agalactiae, Streptococcus anginosus, Streptococcus equinus, Streptococcus bovis, Clostridium perfringens, Enterococcus faecalis*, and *Enterococcus faecium*.

Non-limiting examples of Gram-negative bacteria include *Escherichia coli, Salmonella bongori, Salmonella enterica, Citrobacter koseri, Citrobacter freundii, Klebsiella pneumoniae, Klebsiella oxytoca, Pseudomonas aeruginosa, Haemophilus influenzae, Neisseria meningitidis, Enterobacter cloacae, Enterobacter aerogenes, Serratia marcescens, Stenotrophomonas maltophilia, Morganella morganii, Bacteroides fragilis, Acinetobacter baumannii* and *Proteus mirabilis*.

Clinically relevant fungi may include yeasts, particularly of the genus *Candida*, and fungi in the genera *Aspergillus, Fusarium, Penicilium, Pneumocystis, Cryptococcus, Coccidiodes, Malassezia, Trichosporon, Acremonium, Rhizopus, Mucor* and *Absidia*. Of particular interest are *Candida* and *Aspergillus*. Non-limiting examples of fungi include *Aspergillus fumigatus, Candida albicans, Candida tropicalis, Candida glabrata, Candida dubliensis, Candida parapsilosis*, and *Candida krusei*.

A "non-microbial cell" is accordingly any cell that may be present in a clinical sample which is not a microbial cell. Particularly, in the case of a clinical sample such a cell may be derived from the subject under test (i.e. the subject from whom the clinical sample is taken). In other words, a non-microbial cell may be a cell from a host or test subject. A non-microbial cell may be a non-microbial eukaryotic cell, particularly an animal (i.e. a human or non-human animal) cell e.g. mammalian cell.

A feature of the method is that the recovered microbial cells are viable, i.e. the buffer solution/protease(s) do not substantially harm or damage the microbial cells present in the complex sample and/or prevent or retard the subsequent growth of the microbial cells. The term "viable" defines microbial cells which are able to grow and/or reproduce. The term "viability" refers to the ability of microbial cells to grow and/or reproduce. Thus, according to the present invention the viability of the microbial cells present in a sample is not substantially reduced as a result of the methods used to recover the microbial cells from the sample. It will be understood, of course, that in any biological system absolute effects cannot be guaranteed, and that there will inevitably be some variability. It is accordingly not a requirement that absolutely all microbial cells present in the sample are recovered in a viable state, but rather that substantially all (i.e. a significant majority) or a substantial or significant proportion of recovered cells are viable.

Viability may be quantified as a measure of the percentage of cells which are capable of growth and/or reproduction. Preferably all (i.e. 100%), or substantially all of the microbial cells recovered from a sample may be viable following treatment according to the invention, and it is preferred that at least 99%, 98%, 97%, 96%, 95%, 94% 93%, 92%, 91%, 90%, 85% or 80% A of microbial cells recovered from a sample are viable following filtration. However, the recovery methods described herein may still be of use in the event that at least 75%, 70%, 60%, or 50% of the recovered microbial cells are viable. Although less desired, in certain embodiments of the invention it may suffice for the viable cells recovered from the sample to represent only a fraction of the microbial cells in the sample and the present method may be performed if at least 40%, 30%, 20% or 10% of the total microbial cells which are recovered are viable.

Alternatively, viability may be assessed with respect to the number of viable cells in the buffer solution/protease/sample mixture (i.e. before or without recovery of the microbial cells from the filter in step (d). Thus viability may be determined based on the effect of the buffer solution and proteases on the sample. In certain embodiments, all (i.e. 100%), or substantially all of the microbial cells present in the buffer solution/sample mixture may be viable following contact with the buffer solution in step (b) of the method, and it is preferred that at least 99%, 98%, 97%, 96%, 95%, 94% 93%, 92%, 91%, 90%, 85% or 80% of microbial cells present in the buffer solution/sample mixture are viable after incubation. However, as above the level of viability may be less, e.g. at least 75%, 70%, 60%, 50%, 40%, 30%, 20% or 10% of the microbial cells present in the buffer solution/sample mixture may be viable.

Although, the treatment of the sample with the buffer solution and protease(s) according to the invention may result in high or very high viability of microbial cells in the buffer solution/protease/sample mixture, the recovery of viable microbial cells from the filter in step (d) may of course be less, e.g. due to losses of microbial cells during filtration and/or during recovery from the filter. Thus a lower % of recovery of viable cells from the filter (for example in terms of CFU recovered from the filter compared to CFU in the starting sample) is not in itself indicative that the buffer solution and protease(s) (i.e. in the contacting/incubation step) are detrimental to viability. Thus, in certain embodiments the % of viable microbial cells recovered, as stated above, may alternatively be the % of viable microbial cells which are recovered relative to the total number or amount of microbial cells recovered, Alternatively expressed, in some embodiments the viable cells which are recovered represent at least 90%, 85%, 80%, 75%, 70%, 60%, 50%, 40%, 30%, 20% or 10% of the total microbial cells (or of the total viable microbial cells) present in the starting complex sample.

Viability may be assessed by measuring the growth rate of a microbial culture that has been processed according to the present method and comparing to a microbial culture that has not been processed. Processing a sample to recover microbial cells may have an effect on the rate of microbial growth, however it is preferred that this will not have any significant effect on the rate of microbial growth. However, microbial cultures having at least 90%, 80%, 70%, 60%, 50%, 40%, 30%, 20% or 10% the growth rate of a culture that has not been processed in this way may still be used as a microbial culture preparation for use in determining antibiotic susceptibility of a microorganism.

The complex sample may be any sample containing or suspected of containing microbial cells, and comprising further components (which components may prevent accurate testing of microbial cells present in the sample) that it may be desirable to remove from the sample. A complex sample may typically be, or may comprise, a biological sample or alternatively expressed a complex sample may comprise biological material. In particular, the sample may comprise biologically-derived non-microbial (e.g. cellular) material. The sample may thus be an environmental sample, such as a water sample (e.g. waste water), sewerage effluent, soil sample or suspension, food sample (such as fruit or vegetable juice, meat, fruit, vegetables or dairy products) or homogenate thereof, or a medical or clinical sample.

The complex sample may be treated or processed before being subjected to the method of the invention. In particular, a medium may be added to a sample which is collected (which includes that the sample which is collected may be added to a medium). Such a medium may for example be a carrier or diluent medium. Thus in certain embodiments of the present invention, a sample which is collected may be diluted or collected in a liquid or solution such as water or buffer or other aqueous solution. In certain embodiments the medium will not include a chaotrope or detergent (or any lytic agent as discussed further below). In other embodiments if a detergent or chaotrope is included, or if the medium is hypotonic, the sample will be processed such that in step (b) when the buffer solution and protease(s) are added to the sample no chaotrope or detergent is present in the buffer solution/protease/sample mixture and the mixture is not hypotonic. In another preferred embodiment the medium may be a culture medium (i.e. a medium which permits the growth of microorganisms which may be present in the sample). Accordingly, in a certain particular embodiment, a sample, e.g. a clinical sample, may be collected in a vessel containing culture medium suitable for culturing microbial cells.

In a preferred embodiment of the present invention the sample is or comprises a clinical sample, which may be obtained from a test subject. The test subject (or subject under test) which generally will be a human patient but may be any human or animal, generally mammalian, subject. It may thus be any clinical sample comprising a mixture of non-microbial cells (i.e. cells derived from the test subject), and microbial cells, and may be any sample of body tissue, cells or fluid, or any sample derived from the body, e.g. a swab, washing, aspirate or rinsate etc. Suitable clinical samples include, but are not limited to, blood, serum, plasma, blood fractions, joint fluid, urine, semen, saliva, faeces, cerebrospinal fluid, gastric contents, vaginal secretions, mucus, a tissue biopsy sample, tissue homogenates, bone marrow aspirates, bone homogenates, sputum, aspirates, wound exudate, swabs and swab rinsates e.g. a nasopharyngeal swab, other bodily fluids and the like. In a particularly preferred embodiment, the clinical sample is a blood or a blood-derived sample, e.g. serum or plasma or a blood fraction.

The microorganism may be any pathogenic microorganism or any microorganism causing an infection in the body, and thus the method may be used in the context of detecting or diagnosing a microbial infection in or on any part of the body of a test subject (i.e. any microbial infection) and the nature of the sample (i.e. the clinical sample) may be determined accordingly, e.g. according to the presentation of symptoms of the infection or suspected infection, or the general clinical condition of the subject. Although any microbial infection is encompassed, the method of the invention has particular utility in the detection or diagnosis of sepsis (or more generally management of sepsis), or where sepsis is suspected. Thus, in a particular aspect of the present invention the sample is or comprises a clinical sample, which may be from a subject having, or suspected of having, or at risk of, sepsis. In such a case the sample will generally be blood or a blood-derived sample. Typically the sample will be blood.

In one aspect of the present invention, a clinical sample (e.g. a blood sample) may be collected in a culture flask containing culture medium, and optionally cultured prior to recovery of the microbial cells. It may in some embodiments be desirable to introduce a clinical sample into a culture flask and immediately or after only a short period of culture to remove an aliquot of the clinical sample/culture medium mixture from the flask for testing (e.g. for microbial ID), whilst subjecting the culture flask to continued culture, before further testing (e.g. AST testing). Such a method is described in our co-pending application PCT/EP2015/063173. The microbial cell recovery method of the present invention may be used to recover microbial cells from aliquots removed from such a clinical sample/culture medium mixture before, during or after a period of culture.

Culture medium provided in a culture flask may contain components which neutralise the effects of antimicrobial compounds, e.g. by adsorption to reduce their efficacy and/or concentration in the sample, and/or compounds such as Sodium Polyanethole Sulfonate (SPS) which inhibit the antimicrobial activity of components of a subject's innate immune system (e.g. complement or other factors) that might be present in the sample (Palarasah, Y. et al. J Clin Microbiol. 2010 March; 48(3): 908-914). Separation of microbial cells from culture medium containing compounds such as these may therefore be desirable prior to subsequent testing of the microbial cells.

In a particular aspect of the present invention, the clinical sample is blood or a blood-derived sample, and is collected in a blood culture flask (BCF). Examples of blood culture flasks include a BacT/ALERT (Biomerieux) blood culture flask, a Bactec blood culture flask (Becton Dickinson) or VersaTrek blood culture flask (Thermo Fisher), or indeed any tube, flask or bottle known for the sampling of blood, particularly for the purpose of culture to detect microorganisms.

A complex sample according to the invention may accordingly comprise a clinical sample in a culture medium. Further the complex sample may be a clinical sample culture (i.e. a clinical sample which has been cultured for a period of time). It will be seen in this respect that the complex sample which is subjected to the method of the invention may be a portion of a complex sample which is collected or prepared. Thus the complex sample of the method of the invention may in one embodiment be an aliquot (e.g. a test aliquot) taken or removed from the complex sample e.g. from the contents of a culture vessel (flask) containing a clinical or other sample, whether before, during or after a period of culture (i.e. incubation). Thus in one particular embodiment the present invention provides a method of recovering microbial cells from a blood culture flask, preferably wherein a clinical sample has been cultured for a period of time in a blood culture flask.

Certain commercially available culture vessels (e.g. blood culture flasks) are provided with resin beads, which resin neutralise the effect of any antimicrobial agents which are present in the clinical sample (i.e. which had been administered to the subject under test) in order to facilitate the growth of the microbial cells in culture. In a preferred embodiment, the complex sample may be filtered in order to remove any resins that may be present in the complex sample (e.g. that may have been removed from the culture vessel when a test aliquot is removed). Thus the complex sample may be pre-filtered before the buffer solution is added. Alternatively it may be pre-filtered after the buffer solution is added, and before the sample is filtered. In an alternative embodiment, the resins may be removed by filtration after the microbial cells have been recovered from a filter. In other words, the resins may be removed following recovery of the microbial cells from the filter. Preferably, the step of filtration or pre-filtration to remove resin will utilise a filter having a pore size which does not substantially remove any cellular matter from the test aliquot, but which can remove the resin particles, e.g. at least 100, 200 or 300 μm but could be up to 1000 μm.

The buffer solution is used in the methods of the present invention together with one or more proteases, which improve the filterability of the sample. The term 'protease' is used broadly herein to include any protease, peptidase or proteinase and refers to any enzyme capable of catalysing the hydrolysis of a peptide bond between two L-α amino acids in a polypeptide (i.e. a protein or peptide). A protease may cleave a peptide bond within a polypeptide, i.e. an internal peptide bond (an endopeptidase), or may degrade the terminal or penultimate amino acid (an exopeptidase) from the N-terminal (aminopeptidase) of-C-terminal (carboxypeptidase) end of a polypeptide. Any protease having proteolytic activity within the pH range utilised in the methods of the present invention may be used in the methods of the present invention. In one embodiment, a protease may have its highest activity (i.e. 100% activity) within the pH range of the present invention. However, proteases having their optimal pH (i.e. the pH at which they have a maximum level of activity) outside this range may also be used in the methods of the present invention, provided they retain at least a degree of proteolytic activity within this pH range. A protease which may of used in the methods of the present invention may therefore have at least 90%, 80%, 70%, 60%, 50%, 40%, 30%, 20%, 10% 9%, 8%, 7%, 6% or 5%, activity within the pH range of the buffers described herein, provided a degree of proteolytic activity is retained. Proteases which may be useful for performing the present invention include proteases of the serine, cysteine, aspartate, threonine, glutamic acid or metalloprotease classes. A non-limiting list of proteases which may be of particular utility in the methods of the present invention thus include proteinase K, trypsin, chymotrypsin, elastase, subtilisin, papain, caspase, TEV protease, pepsin, presenilin, alkaline protease, nagarase or protease XV. In a representative example the protease(s) may be or may include proteinase K.

The volume of the buffer solution to be added to the sample will vary depending on the nature of the sample, and/or whether the sample was diluted in a medium (e.g. a culture medium), and the concentration of the various components of the buffer solution. However, in certain aspect a ratio of buffer solution:complex sample of up to 10:1, 5:1, 2:1 or 1:1 may be used. Smaller volumes of buffer solution may alternatively be used, and thus the ratio of buffer solution:complex sample may be up to 1:2, 1:5 or 1:10 may be used. The ratio of buffer solution:complex sample may also fall within the certain ranges, e.g. 10:1-1:10, 5:1-1:5 or 2:1-1:2. In a particularly preferred aspect, however, the ratio of buffer solution:complex sample is 2:1. The buffer solution referred to here may be a buffer solution containing one or more proteases or the volumes and ratios stated may apply to the total volume of buffer solution and protease(s).

The buffer solution used in the methods of the present invention has a pH of at least pH 6.0, more particularly at least pH 6.5, 7.0, 7.5, 8.0, 8.5 or 9.0, and less than pH 11.0. In certain embodiments, the pH may be less than pH 10.7, or less than or equal to pH 10.6, e.g. less than pH 10.6. In a particular embodiment, the pH may be at least pH 6.0 and up to pH 10.5. The pH of the buffer solution may therefore be at least pH 6.5, pH 7.0, 7.5, pH 8.0, pH 8.5 or pH 9.0 and up to pH 10.5 or 10.6. In another embodiment, the pH of the buffer solution may be up to pH 10, up to pH 9.5 or up to pH 9. Accordingly, in certain aspects of the present invention buffer solutions having pH ranges of pH 6.0-pH 10.6, pH 6.0-pH 10.5, pH 6.5-pH 10.5, pH 7.0-pH 10.5, pH 7.5-pH 10.5, pH 8.0-pH 10.5, pH 8.5-pH 10.5 or pH 9.0 to pH 10.5 may be used. It was found that although good filterability was observed at pH values within the ranges outlined above, at pH values above pH 9 the sample was easier to filter (the sample was filtered more quickly and with lower back-pressure). Without wishing to be bound by theory, it is hypothesised that at higher pH values (i.e. above pH 9), a greater degree of lysis of the non-microbial cells may be taking place, thereby allowing the sample to be filtered more easily.

The pH ranges discussed above relate to the pH of the buffer solution that is used in step (b) i.e. of the buffer solution before it is added to the sample. This may be a buffer solution containing protease(s). Alternatively the pH ranges set out above may be applied to a mixture obtained by mixing a buffer solution with one or more proteases (e.g. by premixing a buffer solution and a protease solution or by reconstituting a protease preparation). Further, the pH ranges set out above may alternatively be applied to the buffer solution/protease/sample mixture after the buffer solution and protease(s) are contacted with the sample. In other words the resulting mixture produced in step (b) may have a pH in the ranges set out above. Furthermore, the method may include adjusting pH at one or more times or stages during step (b). For example, the pH of the mixture produced in step (b) may be adjusted, e.g. such that it falls within any of the ranges set out above. pH may be adjusted after all the components (buffer solution, sample, protease(s)) of the mixture have been added, or it may be adjusted after or when (e.g. during) the addition (contact with) one or more of the components. pH adjustment may take place accordingly to procedures well known in the art, e.g. by adding acid or alkali.

The buffer solution will preferably contain a sufficient quantity or concentration of a suitable (e.g. biological) buffer that the pH is maintained upon addition to the sample, i.e. such that the mixture of the sample and the buffer solution is maintained within the desired pH range to allow for the efficient filtration of the sample. The concentration of buffer in the buffer solution may be at least 10 mM, 20 mM, 50 mM, 100 mM, 200 mM, 500 mM, 1M, 2M, 5M or 10M. It will be understood that the buffer solution is an aqueous buffer solution.

Typically a buffer having a pKa of within the range between 7 and 11 may be used to buffer a solution to a pH within the pH range outlined above, and thus in one embodiment the buffer has a pKa within this range. However, other buffers may also be suitable to maintain a suitable pH.

It is also necessary to consider factors such as the solubility of the buffer (more soluble buffers may be used to prepare concentrated stock solutions), permeability of biological membranes to the buffer (permeable buffers may under certain circumstances disrupt water transport across a biological membrane, which can lead to lysis), and the ionic strength of the buffer. Many inorganic substances originally used as buffers (e.g. phosphate) are not biologically inert, and may affect biological systems (e.g. by inhibiting enzyme activity). So-called 'Good' buffers (N-substituted taurine or glycine buffers) are typically biologically inert and are thus considered to be better biological buffers (Biological Buffers, Applichem, 2008, hereby incorporated by reference in its entirety). Thus in one aspect, the buffer may be a 'Good' buffer or a biological buffer.

A number of different buffers may be used in the methods of the present invention, including (but not limited to) the following buffers: ACES, ADA, Ammonia, AMP, AMPD, AMPSO, BES, Bicine, BIS-Tris, BIS-Tris-Propane, Boric acid, Cacodylate, CABS, CAPS, CAPSO, bicarbonate/carbonate, CHES, Citrate, DIPSO, Glycine, Glycerylglycine, HEPES, HEPPS, HEPPSO, Imidazole, MOPS, MOPSO, phosphate, PIPES, POPSO, TAPS, TAPSO, Taurine, TEA, TES, Tricine or Tris. However, in a preferred aspect of the present invention, the buffer is CAPS.

Optionally, one or more nucleases may further be used in the method of the invention. In particular, step (b) may optionally further comprise contacting the sample with one or more nucleases. For example, the buffer solution may optionally further comprise one or more nuclease enzymes. Alternatively, nuclease(s) may be included in a protease preparation or they may be separately contacted with the sample, e.g. separately reconstituted with a buffer solution, or other aqueous solution, and contacted with the sample or a separate nuclease solution may be used. The term 'nuclease' refers to any enzyme capable of catalysing the hydrolysis of a phosphodiester bond between two adjacent nucleotide bases, and includes deoxyribonuclease (DNase) and/or ribonuclease RNase enzymes. The enzymes may cleave a phosphodiester bond within an oligonucleotide molecule (an endonuclease) or may degrade the 3' terminal nucleotide from the end of a nucleotide molecule. Nucleases may be useful in breaking down any nucleic acid which is released from the lysis of non-microbial cells present in the complex sample.

In other embodiments, however, nucleases are not included or used, that is neither the buffer solution, nor the protease preparation, nor any other preparation or reagent contacted with the sample comprises a nuclease, particularly a DNase. In other words, in some embodiments the sample is not contacted with a nuclease, or more specifically a DNase, or even more specifically DnaseI. In certain embodiments, the buffer solution does not comprise a DNase enzyme, e.g. an exonuclease, and/or an endonuclease such as DNaseI.

Other components or ingredients which may be used, e.g. added to or included in the buffer solution include one or more filter aids. Various materials for use as filter aids are known in the art (see e.g. U.S. Pat. No. 7,547,526 (Purdue Research Foundation) and EP1527172 (Molzym)) and any of these may be used, including for example diatomaceous earths or perlites. The amount of filter aid added can be optimised depending on sample type etc.

In certain embodiments the buffer solution utilised in step (b) in the present invention does not contain any added lytic agents or any further ingredients or components which promote the selective lysis of non-microbial cells present in a complex sample. That is the buffer solution does not contain any other such lytic agents, or any such lytic agents beyond the buffer solution itself. (As noted above, the buffer solution may itself in some embodiments have lytic properties, or be capable of lysing (more particularly selectively lysing) non-microbial cells), even if not fully or completely. Thus in certain embodiments, the method of the invention does not utilise any other lytic agents beyond the buffer solution, or beyond the buffer solution and protease(s) and optionally nucleases discussed above, The buffer solution in step (b) therefore does not contain any detergents, including anionic, cationic, non-ionic or zwitterionic detergents. More generally the method does not use, or does not include the use of, a detergent in step (b). Detergents may include one or more non-denaturing lytic detergents, such as Triton X100-R, Triton X-114, NP-40, Genapol C-100, Genapol X-100, Igepal CA 630, Aslasolve 200, Brij 96/97, CHAPS, octyl β-D-glucopyranoside, saponin and nonaethylene glycol monododecyl ether (C12E9, polidocenol). Further detergents which are excluded from the buffer solution include sodium dodecyl sulphate (SDS), N-laurylsarcosine, sodium deoxycholate, bile salts, hexadecyltrimethylammonium bromide, SB3-10, SB3-12, amidosulphobetaine-14 and C7BzO. The buffer further does not comprise a solubiliser, such as Brij 98, Brij 58, Brij 35, Tween 80, Tween 20, Pluronic L64, Pluronic P84, non-detergent sulphobetaines (NDSB 201), aphipols (PMAL-C8), and methyl-β-cyclodextrin, or polyoxyethylene detergent detergents such as polyoxyethylene detergent (which can comprise the structure C12-18/E9-10, wherein C12-18 denotes a carbon chain length of 12 to 18 carbon atoms and E9-10 denotes from 9 to 10 oxyethylene hydrophilic head groups. For example, the polyoxyethylene detergent can be selected from the group consisting of Brij 97, Brij 96V, Genapol C-100, Genapol X-100, nonaethylene glycol monododecyl ether (polidocanol), or a combination thereof and ethylene-diaminetetraacetic acid (EDTA). Molecules such as saponins and choline, or any other small organic molecules which disrupt, disperse or solubilise the phospholipid bilayer of a non-microbial cell may also be considered to be detergents for the purposes of the present invention, and in certain embodiments the buffer solution used in step (b) in the methods disclosed herein does not contain any of these compounds.

Furthermore, the buffer solution further does not contain a chaotrope or chaotropic agent (or more generally step (b) of the method does not use, or include the use of, a chaotrope or chaotropic agent). Chaotropic agents are molecules that can disrupt the hydrogen bonding network between water molecules in a solution, thereby decreasing the hydrophobic effect within the solution. Chaotropic agents include compounds such as butanol, ethanol, phenol, propanol, lithium perchlorate, lithium acetate, magnesium chloride, guanidinium chloride, thiourea and urea.

In certain embodiments the buffer solution further does not contain an ionic liquid. Ionic liquids have been used in the separation of microbial cells from a complex sample or medium (as described in WO 2010/145754), at a preferred range of 0.5-20% w/w. Ionic liquids or liquid salts are ionic species which consist of an organic cation and a generally inorganic anion (i.e. they do not contain any neutral molecules), and usually have melting points below 373 K (preferably being liquids which are ionic at room temperature—approximately 25° C. In general, ionic liquids have the formula $K^+A^-$. The cation $K^+$ of the ionic liquid may be, for example, ammonium, phosphonium, uronium, thiouronium, imidazolium, morpholinium or guanidinium, or a heterocyclic cation. The anion $A^-$ may be, for example, a halide, tetrafluoroborate, hexafluorophosphate, cyanamide, thiocyanate or imides of the general formula $[NR_f)_2]^-$ or of the general formula $N(XR_f)_2]^-$, where $R_f$ denotes partially or fully fluorine-substituted alkyl having 1 to 8 C atoms and X denotes $SO_2$ or CO.

In particular the buffer solution contains neither an ionic liquid nor $MgCl_2$ (although it will be appreciated that de minimus concentrations of $MgCl_2$ e.g. derived from the storage medium of the protease and/or present as an impurity in water used to prepare the buffer solution may be present). In other words, the buffer solution is prepared without the addition of $MgCl_2$. Thus, the concentration of $MgCl_2$ is low e.g. less than 10 mM, 50 mM, 100 mM or 200 mM.

It is also a requirement of the present method is that when the buffer solution and protease(s) are added to the sample the resulting mixture is non-hypotonic. Thus, the tonicity of the buffer solution may be selected or adjusted prior to its addition to the sample so that the addition of the buffer solution to the complex sample would not lead to the hypotonic lysis of the non-microbial cells in the complex sample. Put another way, the buffer solution will be prepared such that the tonicity of the mixture of the complex sample and the buffer solution relative to the intracellular tonicity of non-microbial cells in the sample is within a range which does not result in hypotonic lysis of non-microbial cells. The same applies to any protease and/or nuclease containing solution. By way of example, the osmolarity of NaCl in blood plasma is approximately 290 mOsm/l (equivalent to approximately 154 mM, or 9 g/l NaCl). Hypotonic lysis of human erythrocytes has been reported where the NaCl concentration is below 60 mM (Arias, M. et al. Biochimica et Biophysica Acta (BBA)—Biomembranes Volume 1798, Issue 6, June 2010, pages 1189-1196). In one embodiment of the present invention, the buffer solution contains at least 60 mM NaCl or equivalent concentration of other salt(s) or solutes which results in a solution of similar or equivalent tonicity.

Calculating the osmolarity of a solution may be performed using the formula: Osmolarity=$\Sigma \varphi_i n_i C_i$, where $\varphi$ is the osmotic coefficient (which varies depending on the degree of dissociation of the solute), n is the number of particles into which a molecule dissociates (e.g. for NaCl, n=2), and C is the molar concentration of the solute.

In one embodiment of the present invention, the buffer solution itself may be hypotonic relative to the tonicity of the non-microbial cells in the sample, i.e. its tonicity may be below 290 mOsm/l. However, depending on the relative volumes of buffer solution and the sample, the tonicity of the sample may be sufficient to avoid hypotonic lysis of the non-microbial cells as a result of the addition of the buffer solution. For example, in certain embodiments of the present invention a clinical sample may be provided in a blood culture flask containing culture medium suitable for the growth of microorganisms; such a medium has a high salt content, and thus addition of a hypotonic buffer solution to such a sample may not necessarily result in a hypotonic solution capable of lysing non-microbial cells present in the sample. Similar comments apply in relation to any protease and/or nuclease containing solution.

However, in a further embodiment of the present invention, the buffer solution itself is not hypotonic. The buffer solution may therefore further comprise suitable concentrations of inorganic salts, sugars and/or other small organic molecule (such as an amino acid, carboxylic acid or glycerol etc.) that it is not hypotonic, i.e. it may have an osmolarity of at least 120 mOsm/l, preferably at least 150 mOsm/l, 200 mOsm/l, or 250 mOsm/l. For example, the buffer solution may be isotonic, i.e. its osmolarity may be between the range of 150-400 mOsm/l, 200-350 mOsm/l, or 250-300 mOsm/l. The buffer solution may alternatively be hypertonic, i.e. its osmolarity may be at least 300 mOsm/l, 350 mOsm/l, 400 mOsm/l or 450 mOsm/l. Likewise in embodiments of the invention solutions containing protease and/or nuclease enzymes are similarly not hypotonic.

The osmolarity of the buffer solution itself will depend on the nature of the complex sample, and on the relative volumes of buffer and the complex sample. Thus, in certain embodiments, the buffer solution itself will not be hypotonic. The osmolarity of the buffer solution (and optionally the osmolarity of any protease and/or nuclease solutions) may therefore be selected depending on the nature of the complex sample.

Advantageously, the present invention provides methods which improve the filterability of a clinical sample, i.e. the volume of a clinical sample that can be filtered before the filter becomes 'clogged', i.e. impermeable to any further filtration without risking rupturing the filter membrane is increased. As noted previously, the larger the sample volume which that can filtered, the greater the number of microbial cells may be recovered for further analysis. Thus the volume of the clinical sample which may be filtered may be at least 1 ml, and in certain embodiments of the present invention at least 2 ml, 5 ml, 10 ml, 15 ml, 20 ml, 30 ml, 40 ml or 50 ml.

Any filter material suitable for retaining microbial cells may be used in the methods of the present invention. Filters may be mesh-filters made up of a mesh of fibres, or may comprise defined pores, produced e.g. by etching. In particular, a membrane filter may be used. The filter may be a mesh filter or a depth filter, which has tortuous paths. Mesh or depth filters are typically made of nylon, PVDF or cellulose. The pore structure in a depth filter is the result of stacking layers of porous materials. By design, the interconnected pore structures of these type of membrane filters retain materials, including cells (e.g. microbial cells), by entrapment. This may make recovery of microbial cells from these types of filter more difficult, but does not preclude their use. Indeed, as shown in the Examples below, depth or mesh filters may successfully be used in the methods of the invention. A screen filter (e.g. a polycarbonate membrane filter) has a more uniform pore size distribution and straight pathways through the membrane. This type of filter may be less likely to entrap cells larger than the average pore size. Filters with defined pores (produced e.g. by etching) are known in the art to have increased potential to filter larger volumes. However, such filters are also known to withstand lower pressure during filtration. Filters able to withstand higher pressures may be more desirable. The selection of filter material may therefore be based on several competing factors, depending on the nature of the sample, and/or the microbial cells present therein. However, example filter materials which may be selected for use in the methods of the present invention include Polycarbonate track etched (PCTE), Cellulose acetate (CA), Regenerated Cellulose Acetate (RC), Polyamide/nylon (PA/NY), Polyethersulfone (PES), Asymmetric polyethersulfone (PES), Polyvinylidene difluoride (PVDF), Polytetrafluoroethylene (PTFE), Polytetrafluorethylene (PTFE HP), Polyester track etched (PETE), Polypropylene (PP), Nitrocellulose mixed ester (MCE/CME), and Cellulose nitrate (CN). In a preferred embodiment of the present invention, the filter is a polyamide or nylon filter.

In a particular embodiment, the filter is not a hollow fibre filter. In yet a further aspect, the filter is not pre-treated or coated with an affinity binding agent or moiety having affinity for a microbial cell prior to filtration of the sample. Thus, in such an embodiment the filter is not designed or configured for selective capture of microbial cells by use of an affinity binding agent for microbial cells.

The filter will have a pore size suitable for the recovery of microbial cells from a solution. Preferably, the filter will have a pore size of less than or equal to 0.6 μm, more preferably less than or equal to 0.5 μm, 0.4 μm or 0.3 μm. In a particular aspect of the present invention, the pore size of the filter is or is less than 0.2 or 0.22 μm.

Following retention of the cells by the filter (i.e. on and/or in the filter), the cells may be subjected to one or more further steps to remove non-microbial cells and/or cell debris, prior to further recovery or analysis of the microbial cells. Thus, for example the material (i.e. the cells or the material which contains the microbial cells) which is retained by the filter may be subjected to a step of selective lysis of non-microbial cells, either whilst the cells are on or in the filter (e.g. during washing steps as described below) or during recovery, or the cells/material which are recovered from the filter may be subjected to further step(s), including e.g. selective lysis of non-microbial cells, after they are recovered from the filter, but before analysis or testing of the microbial cells. However, in certain embodiments and for some downstream tests (e.g. molecular tests) any further processing of the retained or recovered cells, for example such as a further step of non-microbial selective cell lysis, may not be necessary and it may be possible to use the recovered cells directly, without such a step.

Thus, following retention of cells by the filter and/or recovery of the cells from the filter, the cells may be subjected to a selective lysis step to lyse non-microbial cells which may be retained or recovered with the microbial cells. Depending on the degree of lysis of the non-microbial cells during step (b) of the present invention, such a step may be viewed as a selective lysis step (e.g. if substantial selective lysis of the non-microbial cells does not take place in step (b)), or may be viewed as a further selective lysis step (e.g. if a substantial portion of the cells are lysed in step (b)).

Microbial cells obtained via the methods of the present invention may be used in tests to determine their identity and/or antimicrobial susceptibility. Such tests may be performed according to any testing techniques which are known in the art and widely described in the literature, including conventional or traditional microbiological identification and AST tests, or any other identification, microbial analysis or characterisation or AST test. Mention may be made of microbial identification methods such as spectroscopy or mass spectroscopy (Farina et al. 2014. New Microbiologica, 38, 245-250).

The microbial cells may be subjected to such analysis or testing methods either with or without further processing of the cells recovered from the sample. Such downstream processing may include e.g. removing non-microbial cells and/or isolating nucleic acid from the microbial cells for genetic tests, as described in more detail below. Selective lysis of non-microbial cells will generally release non-microbial nucleic acids. Accordingly, such downstream processing may also include removal or degradation of such non-microbial nucleic acid, e.g. using nuclease enzymes.

The method of the present invention is particularly suited for use in the microbial detection and testing protocol as described in PCT/EP2015/063173 and GB 1511129.7.

The recovered microbial cells may therefore optionally be cultured and subjected to an antimicrobial susceptibility test assay or a conventional biochemical microbial identification test, and/or genetic material (e.g. DNA) from the microbial cells may be isolated and subjected to one or more molecular tests to identify the microorganism and/or any antimicrobial resistance markers that the microorganism may have.

Subsequent testing of the microbial cells obtained from the sample may be performed with or without an intervening selective lysis step (or further selective lysis step) to lyse non-microbial cells recovered from the complex sample. As noted above, under certain conditions a substantial proportion of the non-microbial cells present in the complex sample may be lysed upon contacting the complex sample with the buffer solution of step (b) of the present method. Thus, depending on the nature of the test which is to be performed and the degree of selective lysis which occurs during step (b) of the present invention, selective lysis of the non-microbial cells which remain following filtration and recovery may be desirable.

Microbial cells obtained from the sample may be subjected to one or more molecular-based genetic tests. In one embodiment, following the filtration step, or during or after recovery of the filter retentate (which includes the microbial cells), non-microbial cells present in the sample (and hence in the retentate/recovered microbial cells) may be selectively lysed and non-microbial genetic material (nucleic acid) may be degraded or removed. Methods for this are well known in the art and indeed commercially available (e.g. from Qiagen or Molzym). In one embodiment, selective lysis this may be performed using one or more chaotropes, in particular chaotropic salts such as guanidinium chloride, guanidinium thiocyanate and/or sodium iodide. Furthermore, one or more surfactants such as sodium dodecyl sulphate, Brij40, Triton X100 and/or Tween-20 may be used. One or more chaotrope-resistant nucleases may be used to degrade genetic material obtained from the non-microbial cells following lysis. Such a selective lysis and degradation of non-microbial nucleic acid may be performed on the filter or after recovery of the retained cells (material) from the filter. Such a step may, however, not be required, and direct recovery of nucleic acids from microbial cells may be performed without such a selective lysis step being performed.

We have determined that certain commercially available DNA isolation methods (e.g. those utilizing chaotrope reagents) cannot be used directly on blood culture flasks (i.e. to recover DNA from a microbial cell in a BCF). The present invention advantageously permits use of such chaotrope-based DNA isolation methods on cells recovered from a from a BCF sample, using the method of the invention.

Microbial cells may be recovered and lysed following recovery from the filter to obtain (release) microbial nucleic acid for subsequent testing. As discussed above, a selective lysis step to remove any non-microbial cells which remain following filtration may or may or may not be performed prior to the release of microbial nucleic acid for subsequent testing. Whilst it will be appreciated that recovery of microbial cells for such a purpose does not require viable microbial cells, it may be advantageous (e.g. in an automated system) for the same microbial recovery process to be used both for recovery of microbial cells for genetic (or molecular testing) and for other tests such as AST or conventional biochemical ID tests which require viable cells. Indeed the recovered microbial cells may be divided into aliquots for different tests. Methods for lysis of microbial cells and recovery of nucleic acid therefrom are well known in the art and such steps may accordingly be performed using any technique known in the art). The microbial nucleic acid thereby obtained may be subjected to one or more molecular tests to identify the microorganism and/or any antimicrobial resistance markers present therein, again using techniques well known in the art.

The recovered microbial cells obtained from the sample may be subjected to antimicrobial susceptibility testing. A culture may be established using the recovered microbial cells, and growth may be monitored under two or more different conditions (e.g. comprising one or more different antimicrobial agents and one or more different concentrations). In a preferred embodiment, microbial growth in the AST test may be monitored by imaging, and thus in one embodiment it may be desirable to remove non-microbial cells and/or cell debris present in the sample, which are recovered along with the microbial cells, as these may interfere with the imaging. Selective non-microbial cell lysis may be performed as described above. It may, in certain embodiments, be desirable to avoid the use of chaotropes for recovery of cells for AST and alternatively, this may conveniently performed by hypotonic cell lysis, e.g. using a buffer that is hypotonic relative to the tonicity of the non-microbial cells present following retention of the cells on the filter or a lytic/detergent containing solution. However, in an alternative embodiment, such a selective lysis step (or further selective lysis step) may not be necessary, and a culture may be established directly using the cells recovered from the filter.

In one embodiment of the present invention, the filter may be subjected to one or more optional wash steps following filtration and prior to recovery of the microbial cells, wherein the cells retained by the membrane are washed with a wash buffer. This may facilitate the subsequent recovery of microbial cells from the filter, remove impurities (e.g. non-microbial cell debris and/or nucleic acids), and/or selectively lyse non-microbial cells which were not lysed during step (b) and thus were retained on the filter following filtration. Thus a step of selective non-microbial cell lysis (or further selective non-microbial cell lysis) may be performed as part of, or during a wash step. The wash buffer may be hypotonic, isotonic or hypertonic relative to the intracellular tonicity of the non-microbial cells, and may optionally comprise one or more detergents, chaotropic agents, nucleases and/or proteases as previously described herein, or any other lytic agent. Multiple or repeated (i.e. more than one e.g. two, three, four or more) wash steps may be performed, e.g. in an iterative manner.

Washing of the retentate may be performed by adding the wash buffer in the same flow direction through the filter as the sample and buffer solution or sample/buffer solution mixture or it may be added by back flushing through the filter and then filtering through the filter.

Cells retained by the filter (i.e. the retentate) are recovered following removal of the liquid fraction (filtrate) from the clinical sample. Recovery may be achieved by back-flowing (i.e. flowing in the opposite direction to filtration) a liquid or aqueous medium e.g. a buffer (e.g. phosphate-buffered saline (PBS), Tris-buffered saline (TBS) or HEPES-buffered saline (HBS) or microbial growth medium (e.g. Mueller Hinton media) through the filter. Alternatively, cells may be mechanically removed from the filter surface or from within the filter e.g. by vortexing or scraping, or by washing e.g. by repeated pipetting to detach the cells from the filter. Alternatively, the filter may be removed from the filtration apparatus and placed in a suitable buffer or growth medium in order to allow the cells to desorb from the filter.

It will be seen that one or more of the further purification steps outlined above may be performed directly on the cells retained by the filter, i.e. as part of or during the course of a wash step. The wash buffer may thus in one embodiment be a selective lysis buffer, as described above. However, in an alternative embodiment, where such further purification steps are performed, these may be performed following the recovery of the cells from the filter, i.e. on microbial cells resuspended or recovered from the filter.

It will be seen that as well as the buffer solution of step (b) other buffers may be used in the methods of the invention, e.g. a wash buffer, or a recovery buffer (e.g. for back-flushing or for resuspending recovered cells) or to in protease and/or nuclease preparations. The buffer solution of step (b) may thus be viewed as a first buffer solution of the method of the invention.

The protease(s) may be added into the (first) buffer solution at any convenient time. In one embodiment a protease will be added to a buffer solution and premixed before adding to the sample. Alternatively, in another embodiment a buffer solution and protease may be added separately to the sample, e.g. simultaneously or sequentially, e.g. one immediately after the other. The protease(s) may be added to a buffer solution immediately or just prior to use. It may be added as a protease solution or as a powder. Similarly, a nuclease (if used) may be added before use. For example a buffer solution without any enzymes (i.e. protease and optionally nuclease) may be prepared and may be added to a freeze-dried (or lyophilised) protease (and optionally nuclease) preparation to reconstitute the enzyme(s) before adding to the sample. Alternatively the protease and/or nuclease enzymes may be separately reconstituted (with the sample buffer solution or with a different buffer solution or aqueous solution) and separately contacted with the sample. In a still further embodiment, the protease and/or nuclease enzymes may be constituted by contact with the sample or with a buffer solution/sample mixture. Thus, the mixture components i.e. sample, buffer solution and protease(s) (and optionally nuclease(s)) may be contacted with one another in any order. pH adjustment may take place at any stage. Wash and recovery buffers may be similarly prepared.

Conveniently, the methods of the present invention may be automated. Various steps of the method discussed above lend themselves well to automation, for example addition of a buffer solution to a complex sample and the subsequent filtration of the sample to retain microbial cells. Resuspension of the cells from the filter following filtration may also advantageously be automated. Complex samples may in certain circumstances represent a biohazard to a user, and thus performing processes or steps such as these in an automated manner (i.e. without repeated exposure of a user to the sample) may be seen as a means to reduce the risk associated with the handling of potentially hazardous samples. The automated recovery of microbial cells from a complex sample therefore has potential time, cost, and safety benefits.

The present invention may therefore be seen to provide a microbial recovery device for the recovery of viable microbial cells from a complex sample, said device being arranged to receive a complex sample of greater than 1 ml, the device comprising: a reservoir comprising a buffer solution containing one or more proteases, or a reservoir containing a buffer solution and a reservoir containing one or more proteases, wherein said buffer solution has a pH of at least pH 6 and less than pH 11, wherein said buffer and said protease(s) do not comprise a detergent or a chaotrope, and wherein the microbial recovery device is arranged for mixing the sample with the buffer solution and proteases to produce a mixture; a filter suitable for retaining microbial cells and arrange to receive and filter the mixture; and a reservoir containing a liquid for recovering viable microbial cells from the filter, the reservoir connected to the filter and the microbial recovery device being arranged to convey the liquid to the filter to remove the retained microbial cells.

The composition of the buffer solution and protease preparation is such that the buffer solution/protease/sample mixture (i.e. the mixture formed by contacting the buffer solution and proteases with the sample) is non-hypotonic, e.g. non-hypotonic with respect to the complex sample (in particular any non-microbial cells present in the sample).

The microbial recovery device may preferably be arranged to perform any or all of the method steps and preferred/optional steps set out above.

The device may comprise a sample chamber for receiving the complex sample. In this case the microbial recovery device may be arranged to add the buffer solution and proteases to the sample before the mixture is conveyed to the filter. The device may alternatively be configured such that the sample is provided directly into the reservoir comprising the buffer solution containing the one or more proteases. Alternatively, the device may be configured such that the sample is provided directly into the reservoir comprising the buffer solution or the reservoir containing one or more proteases. In other words, the reservoir containing the buffer solution and/or one or more proteases may also be a sample chamber. In such an embodiment, the reservoir containing the buffer solution may be directly connected to the filter.

Where the device comprises separate reservoirs containing the buffer solution and one or more proteases, the device may be arranged so that the buffer solution and one or more proteases are combined prior to mixing with the sample, resulting in a buffer solution containing one or more proteases that is then contacted with the sample. Alternatively the device may be arranged so that the buffer solution and one or more proteases may be contacted with the sample separately, e.g. the buffer solution may first be contacted with the sample followed by the one or more proteases, the buffer solution and one or more proteases may be contacted with the sample simultaneously or substantially simultaneously, or the one or more proteases may first be contacted with the sample followed by the buffer solution.

In a particular embodiment, wherein the device contains a reservoir containing a buffer solution and a reservoir containing one or more proteases, the one or more proteases may be provided in a freeze-dried or lyophilised form (e.g. as a solid or as powder). Said freeze-dried at least one protease may be reconstituted in an aqueous solution. In a preferred embodiment, the aqueous solution will be the buffer solution. However, in an alternative embodiment, the aqueous solution may be the complex sample, i.e. the complex sample may be added directly to the freeze-dried one or more protease. In yet another embodiment, the buffer solution may be contacted with the complex sample and the mixture may be used to reconstitute the freeze-dried at least one protease. Preferably the device may further comprise or be capable of being connected to a fluid conveying device to drive the filtration of the sample. This may be e.g. a pump, syringe body or vacuum manifold, but may be any fluid conveying device suitable for driving the filtration of a sample through a filter. This fluid conveying device may be connected to the sample chamber or filter as required in order to drive the filtration of the sample.

The reservoir containing the liquid for recovering microbial cells is connected to the filter. The reservoir may be connected to the opposite side of the filter to the sample chamber, i.e. so that the liquid from the reservoir passes through the filter in the opposite direction to the sample. Microbial cells retained on the filter may thereby be recovered by back-flushing the liquid through the filter. However, in an alternative embodiment the reservoir is connected to the same side of the filter as the sample chamber, and recovery of the microbial cells retained on the filter may be effected by contacting the retentate side of the filter with the liquid without the liquid passing backward through the filter.

The liquid for the recovery of viable microbial cells may be a buffer or culture medium as hereinbefore described. However, in a particular embodiment of the present invention, the liquid is culture medium suitable for the culture of microbial cells, i.e. the device may comprise a reservoir containing culture medium suitable for the culture of microbial cells for recovering viable microbial cells from the filter.

The device may optionally further comprise a reservoir containing one or more nucleases (which nucleases may optionally be freeze-dried and reconstituted prior to use). Said reservoir may be connected to the sample chamber or the reservoir containing the buffer solution and/or at least one protease.

The device may optionally also comprise a reservoir containing a wash buffer for washing the filter after filtration, connected to the filter. The reservoir containing the wash buffer may, in one embodiment, be connected to the same side of the filter as the sample chamber, such that the wash buffer may contact the same side of the filter as the retentate. However, in an alternative embodiment, the reservoir containing the wash buffer may be connected to the opposite side of the filter, such that the wash buffer passes through the filter in the opposite direction to the sample, thereby washing the filter. The wash buffer may be separated from the sample by filtration following washing.

The wash buffer may be of any composition as hereinbefore described. In a particular embodiment, the wash buffer may be a selective lysis buffer suitable for selectively lysis non-microbial cells (in particular cells derived from the subject under test) that are retained on the filter following filtration. In certain embodiments, and as discussed above, the wash buffer may therefore comprise one or more proteases, nucleases, detergents and/or chaotropic agents, and/or may be hypotonic relative to the non-microbial cells in the complex sample. The device may thus optionally further comprise one or more further reservoirs containing one or more proteases, nucleases, detergents and/or chaotropic agents, which reservoirs may be connected to the reservoir containing the wash buffer and/or the sample chamber. Suitable wash buffers may thereby be prepared directly within the device of the present invention.

In one embodiment, the device for recovering microbial cells may be a single-use consumable for recovering microbial cells from a complex sample. The device may therefore be configured to be incorporated into a larger device which comprises means for the culture and/or testing of microbial cells. However, in an alternative aspect the device may be an integrated part of a larger device, and only certain constituent parts of said device, e.g. the filter, may be single-use consumables.

The present invention may be better understood with reference to the following Examples.

EXAMPLES

Samples consisting of BD Bactec BCF media and EDTA blood (25%) spiked with bacteria (*E. coli* or *S. pyogenes*) (approximately $10^6$ CFU/ml) were added to 0.3 M CAPS buffer containing protease in the absence of detergent. 5 ml of the blood/media mixture were added to 10 ml buffer and incubated before filtration by hand using a 0.2 μm filter, diameter 25 mm. After filtration, if the entire volume went through the filter, the filters were washed with 2 volumes of MH medium or PBS. Samples were resuspended to recover cells by back-flushing the filters with 5 ml MH-media or PBS. Filtration time and volume of sample it was possible to filter were measured for each sample. Viability of microbial cells recovered from the membrane was performed on TSA-plates and was recorded as CFU after overnight incubation. Recovery was calculated based on input number of bacteria an output number of bacteria corrected for the varying volume of in and out sample. pH of the buffer was as stated in the Examples below.

Example 1—Addition of a Buffer Containing a Protease to a Sample Enhance its Filterability An initial experiment was performed to determine the effect of the addition of a buffer containing a protease on the filterability of a sample. Samples were prepared using *E. coli* as outlined above and incubated with a buffer solution containing proteinase K, at a range of different pH values. As a comparison, a further sample was incubated with a buffer solution at pH 10.5 which did not contain proteinase K, Results indicating the filterability of each sample following treatment with the respective buffers are shown in Table 1.

TABLE 1

| Sample | pH 9 | pH 9.5 | pH 10 | pH 10.5 | pH 11 | pH 11.5 |
|---|---|---|---|---|---|---|
| Buffer only | — | — | — | <1 ml | — | — |
| Buffer + proteinase K | 15 ml | 15 ml | 15 ml | 15 ml | 15 ml | 15 ml |
| Recovery of viable cells after backflush | 5% | 5% | 20% | 5% | 0% | 0% |
| Viability of cells after incubation (without filtration) | N.D | 100% | N.D | >90% | N.D | <1% |

Samples incubated with buffer solutions containing proteinase K at each of the pH values tested showed enhanced filterability compared with the sample which did not contain a proteinase. This demonstrates that a proteinase may be of use in increasing the filterability of samples A further experiment was conducted to confirm the importance of Proteinase K in enhancing the filterability of a clinical sample. Samples were prepared using *E. coli* as outlined above, and the effect of the addition of buffer with or without proteinase K on the filterability of a sample was assessed using CAPS 0.3M buffer pH 10.5+proteinase K. Results are shown in Table 2.

TABLE 2

| | Did volume pass filter? | Approximate time to filter |
|---|---|---|
| Sample 1 (+Prot K) | All passed | 1 min, 45 sec |
| Sample 2 (−Prot K) | 4.5 ml | 1 min, 22 sec |
| Sample 3 (+Prot K) | All passed | 1 min, 46 sec |
| Sample 4 (−Prot K) | 4.5. ml | 59 sec |

Example 2—Viability of Microbial Cells

Samples were prepared using *E. coli*, a Gram-negative bacterium, and *S. pyogenes*, a Gram-positive bacterium, as outlined above. Samples were contacted with buffer at pH 10.0 containing Proteinase K, followed by a wash with PBS and subsequent treatment with DNaseI for 5 minutes, and cells on the filter were resuspended as outlined above. Viability of the microbial cells recovered from the samples were subsequently tested, and the results are shown in Table 3.

TABLE 3

| | E. coli | S. pyogenes |
|---|---|---|
| Expt. 1 | 13-20% | 31-32% |
| Expt. 2 | 30-34% | 47-56% |
| Expt. 3 | 25-27% | 28-39% |
| Expt. 4 | 32-36% | |
| Average | 27% (n = 12) | 39% (n = 9) |

Both the Gram-negative *E. coli* and Gram-positive *S. pyogenes* were found to be viable at pH 10.0, with *S. pyogenes* appearing to have a greater degree of viability under these conditions.

Recovered cells were also used for preparation of bacterial DNA using the DNA kit from Molzym (Molzym GmbH, Bremen, Germany) and results were quantified with real time PCR for presence of bacterial as well as residual human DNA.

For *E. coli* approximately the total pre-efficiency from added bacteria measured as CFU to bacterial DNA measured as genomic copies present in eluate were about 7% and for *S. pyogenes* around 14%. Human DNA was found to be reduced by a factor of more than 99.9%.

Example 3—the Effect of Filter Material on Filterability

Four filter materials: regenerated cellulose acetate (RegCA) (Ø 25 mm); polyamide (PA) (Ø 25 mm); polyethersulfone (PES) (Ø 30 mm); polyvinylidene (PVD) (Ø 30 mm); were tested and compared to the standard cellulose acetate (CA) (Ø 30 mm). All filters had a pore size of 0.2 μm. Samples were prepared as outlined above using a buffer at pH 10.5 and containing proteinase K. Results are shown in Table 4.

TABLE 4

| | Did volume pass filter? | Approximate time to filter |
|---|---|---|
| PES | 6.5 ml | 3 min 40 sec |
| PVD | All passed | 3 min 26 sec |
| CA | All passed | 4 min 42 sec |
| RegCA | All passed | 6 min 17 sec |
| Polyamide | All passed | 2 min |

This demonstrates that although a range of different filter materials may be used in the methods of the present invention. Polyamide and cellulose acetate filters were selected for further testing to establish the efficiency or recovery of the microbial cells retained on the filter. Recovery of bacteria from different filters is shown in Table 5.

TABLE 5

| | Did volume pass filter | Approximate time to filter | CFU recovered | Recovery efficiency |
|---|---|---|---|---|
| CA (1) | All passed | 2 min 6 sec | 1E+06 | 69.1% |
| PA (1) | All passed | 1 min 50 sec | 1E+06 | 53.1% |
| CA (2) | All passed | 3 min | 1E+06 | 79.1% |
| PA (2) | All passed | 1 min 44 sec | 8E+05 | 45.6% |

A good efficiency of recovery of *E. coli* cells was observed for both the polyamide and cellulose acetate filters.

Example 4—the Effect of pH on Filterability and Viability

Multiple CAPS buffers all at 0.3 M were prepared and adjusted to pH 7, 8, 9, 9.5, 10, 10.5 and 11. Samples were added to each CAPS buffer followed by incubation with Proteinase K. Samples were then filtered using polyamide filters and resuspended using phosphate-buffered saline (PBS) solution. Recovery was calculated based on colony formation (i.e. only viable cells were counted). Filtration and recovery of microbial cells at different pH values is shown in Table 6.

TABLE 6

|  | Did volume pass filter? | Approximate time to filter | CFU recovered | Recovery efficiency |
|---|---|---|---|---|
| BCF |  |  | 2E6 | — |
| pH 9.0 | All passed | 1 min 21 sec | 8E+4 | 4% |
| pH 9.5 | All passed | 1 min 38 sec | 2E+5 | 9% |
| pH 10.3 | All passed | 1 min 58 sec | 5E+5 | 24% |
| pH 10.7 | All passed | 1 min 13 sec | 3E+3 | 0.1% |
| pH 11.0 | All passed | 46 sec | 0 | 0 |
| pH 11.5 | All passed | 32 sec | 0 |  |

An improvement was in filterability was seen for treatment with buffers at pH11-11.5, however, microbial viability at these high pH values was compromised. Following the finding that buffers having pH values of at least pH 9 could be used to enhance the filterability of a clinical sample, buffers having a wider range of pH values were tested for their effect on enhancing the filterability of a clinical sample. The results of this are shown in Table 7.

TABLE 7

|  | Volume filterable pH | | | | | | | |
|---|---|---|---|---|---|---|---|---|
|  | 7 | 7.5 | 8 | 8.5 | 9 | 9.5 | 10 | 10.5 | 11 |
| Buffer only | n/d | n/d | n/d | n/d | n/d | <1.5 ml | n/d | | |
| Buffer + proteinase K | >15 ml | >15 ml | >15 ml | >15 ml | >15 ml | >15 ml | >15 ml | | |
| Recovery of viable bacteria | 22% | 21% | 19% | 8% | 6% | 9% | 20% | 6% | <1% |

These data indicate that the filterability of a clinical sample may be enhanced using a buffer solution containing Proteinase K at a wide range of pH values. Thus a method to allow filtration of large volumes of complex matrices, such as blood and blood+culture media at any pH between pH 7 and less than pH 11 using a protease to facilitate filtration is demonstrated and we believe that such a method may be used with buffers at any pH from pH 6 to less than pH 11. Viability of microbial cells between pH 7 and pH 10.5 was found to be close to 100% as evaluated after incubation with CAPS and proteinase K buffer and direct plating for counting viable count. At pH 7 between 92 to 120% survival was recorded after 5 to 15 minutes proteinase K treatment. At pH 10.5 between 95 to 120% survival was recorded after 10 minutes proteinase K treatment. The over 100% survival can be accounted for imprecision in the plating procedure that was done manually in these experiments. Accordingly, whilst the recovery of viable bacteria is reduced between pH 8.5 and 9.5 in the data in Table 7 above, this may be addressed by optimisation of the particular reaction conditions at each pH, e.g. reaction time, protease concentration etc.

Example 5—Conditions Used for Filtration are Less Harmful to Microbial Cells than Those Used in the Art A further experiment was performed to confirm that the pH of the filtration conditions identified herein are less harmful to microbial cells than those currently in the art. Selective lysis of non-microbial cells has been shown to be possible at very high pH values, however, the viability of the microbial cells under such conditions is poor.

EDTA-blood samples spiked with E. coli were incubated with a buffer solution at pH 10.5 or a solution containing 8% NaOH. A comparison of these conditions with the filtration conditions described herein is provided in Table 8.

TABLE 8

| Sample | Before | 5 ml blood + 10 ml pH 10.5 buffer | 5 ml blood + 5 ml 8% NaOH, pH 14 |
|---|---|---|---|
| CFU/ml | 1E+6 | 5E+5 | 0 |
| Recovery* | — | 123% | 0% |
| CFU/ml | 6E+5 | 2E+5 | 0 |
| Recovery* | — | 103% | 0% |

Incubation of the sample with a solution containing 8% NaOH resulted in no viable microbial cells being recovered from the sample. In contrast, addition of the buffer solution at pH 10.5 did not substantially affect the viability of the microbial cells in the sample. Recovery of over 100% was observed for samples incubated with buffer at pH 10.5 due to viability experiments only being performed in duplicate.

The invention claimed is:

1. A method of recovering viable microbial cells from a complex sample containing non-microbial cells, said method comprising:
   a) providing a sample having a volume of at least 1 ml, wherein where the sample has previously been contacted with a detergent or chaotrope, the sample is processed such that in subsequent steps (b) and (c), no chaotrope or detergent is present;
   b) contacting said sample with a buffer solution and one or more proteases, wherein said buffer solution has a pH of at least pH 6 and less than pH 11, wherein said buffer solution and said one more proteases do not comprise a detergent or a chaotrope, wherein the buffer solution/protease/sample mixture is non-hypotonic to the non-microbial cells, and wherein no detergent or chaotrope is present or used in step (b);
   c) subjecting the mixture produced in step (b), in which no detergent or chaotrope is present, to a filtration step, by filtering the mixture obtained in step (b) through a filter suitable for retaining microbial cells; and d) recovering the microbial cells retained by the filter in step (c), wherein the recovered microbial cells are viable.

2. The method of claim 1, wherein the sample is contacted with the buffer solution and the one or more proteases separately.

3. The method of claim 1, wherein the buffer solution and the one or more proteases are mixed prior to step (b).

4. The method of claim 1, wherein the sample is or comprises a clinical sample.

5. The method of claim 1, wherein the sample is a clinical, biological or environmental sample added to a medium.

6. The method of claim 5, wherein the medium is a culture medium.

7. The method of claim 4, wherein the clinical sample is a blood sample.

8. The method of claim 7, wherein said blood sample is collected in a blood culture flask.

9. The method of claim 1, wherein said protease is proteinase K.

10. The method of claim 1, wherein the pH of the buffer solution is between pH 7 and less than pH 10.7.

11. The method of claim 1, wherein the pH of the buffer solution is between pH 7 and pH 10.5.

12. The method of claim 1, wherein the pH of the buffer solution is between pH 9 and pH 10.5.

13. The method of claim 1, wherein the filter is a membrane filter.

14. The method of claim 1, wherein the filter is a polyamide filter.

15. The method of claim 1, wherein the filter has a pore size of less than 0.4 µm.

16. The method of claim 1, wherein the cells retained on the filter are recovered through back-flushing the filter using a liquid.

17. The method of claim 16, wherein the cells are back-flushed using culture medium.

18. The method of claim 1, wherein said method further comprises one or more wash steps between steps (c) and (d).

19. The method of claim 18, wherein said wash step selectively lyses non-microbial cells retained on the filter.

* * * * *